United States Patent [19]
Nash et al.

[11] 3,960,039
[45] June 1, 1976

[54] COLLET WRENCH

[75] Inventors: John E. Nash, Downingtown; Trevor D. Reader, King of Prussia, both of Pa.

[73] Assignee: Star Dental Manufacturing Co., Inc., West Conshohocken, Pa.

[22] Filed: Aug. 12, 1974

[21] Appl. No.: 496,604

[52] U.S. Cl. .............................. 81/52.4 R; 32/27; 64/29
[51] Int. Cl.² ...................................... B25D 23/142
[58] Field of Search ............. 81/52.4 R, 52.4 A, 55; 32/27; 64/29

[56] References Cited
UNITED STATES PATENTS

| | | | |
|---|---|---|---|
| 1,260,698 | 3/1918 | Moore et al. | 81/55 |
| 2,410,971 | 11/1946 | Hartley | 81/52.4 R |
| 2,634,640 | 4/1953 | Pedersen | 81/52.4 R |
| 3,325,899 | 6/1967 | Staunt | 32/27 |

Primary Examiner—James L. Jones, Jr.
Attorney, Agent, or Firm—Caesar, Rivise, Bernstein & Cohen

[57] ABSTRACT

A collet wrench adapted to place a predetermined force on a collet threadedly secured in a dental handpiece. The wrench comprises a frame and means on the frame for securing the rotor shaft against rotation. A shaft is rotably mounted in the frame, and has a lower end of non-circular cross-section. The lower end is received in the collet and is adapted to rotate the collet relative to the rotor shaft. A disc having ratchet teeth is keyed to the shaft and a second disc having ratchet teeth is placed on the first mentioned disc and held there by a spring force. Rotation of the second disc causes the rotation of the first disc, and the subsequent rotation of the shaft having the end secured to the collet. After a predetermined force has been applied to the second disc, it will slip relative to the first disc, and accordingly apply a predetermined force to the collet. The pressure of the spring controls the predetermined force.

13 Claims, 9 Drawing Figures

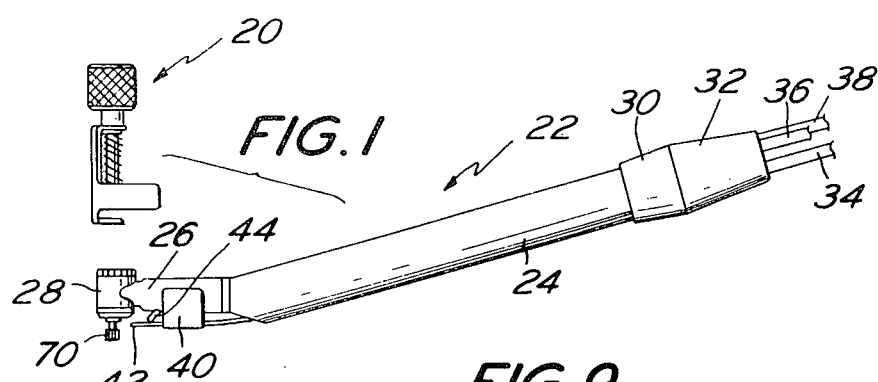
FIG. 1
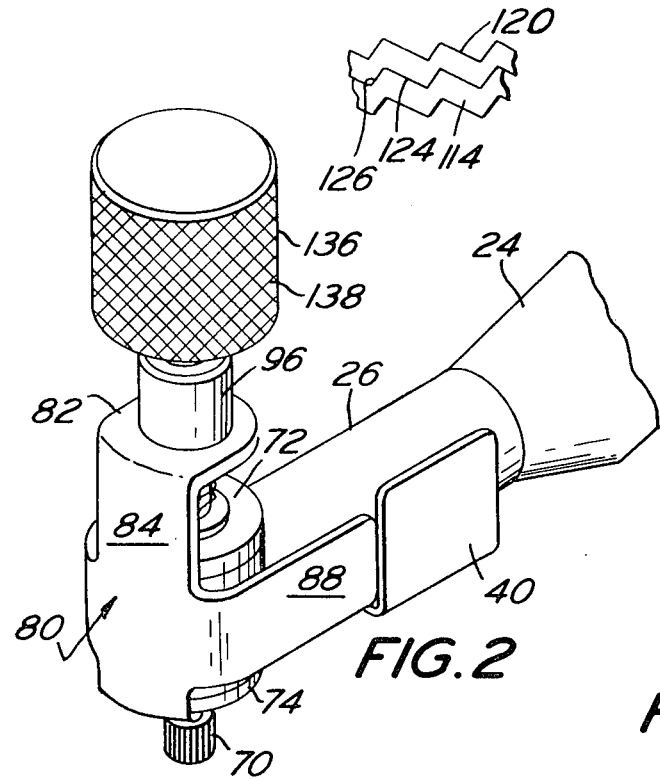
FIG. 2
FIG. 9
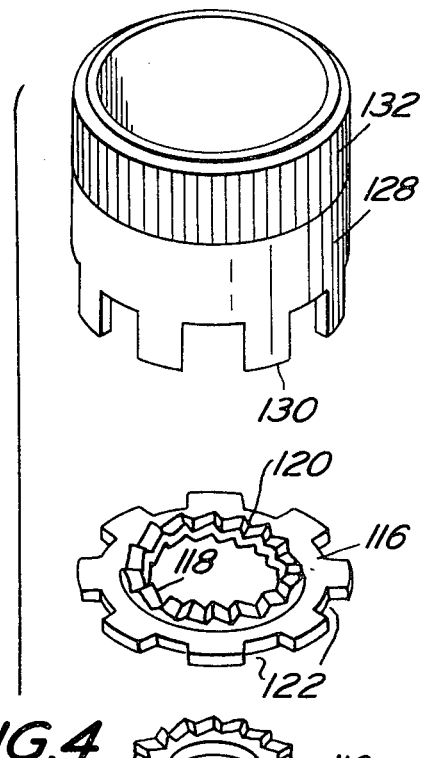
FIG. 4
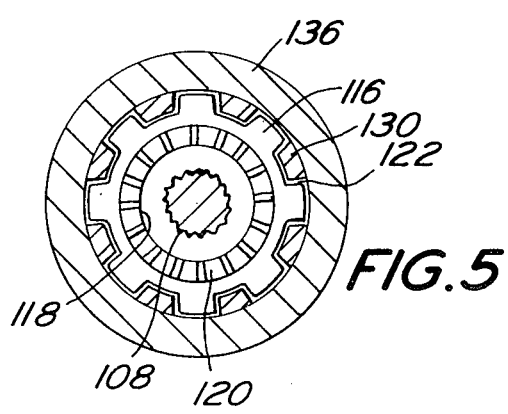
FIG. 5

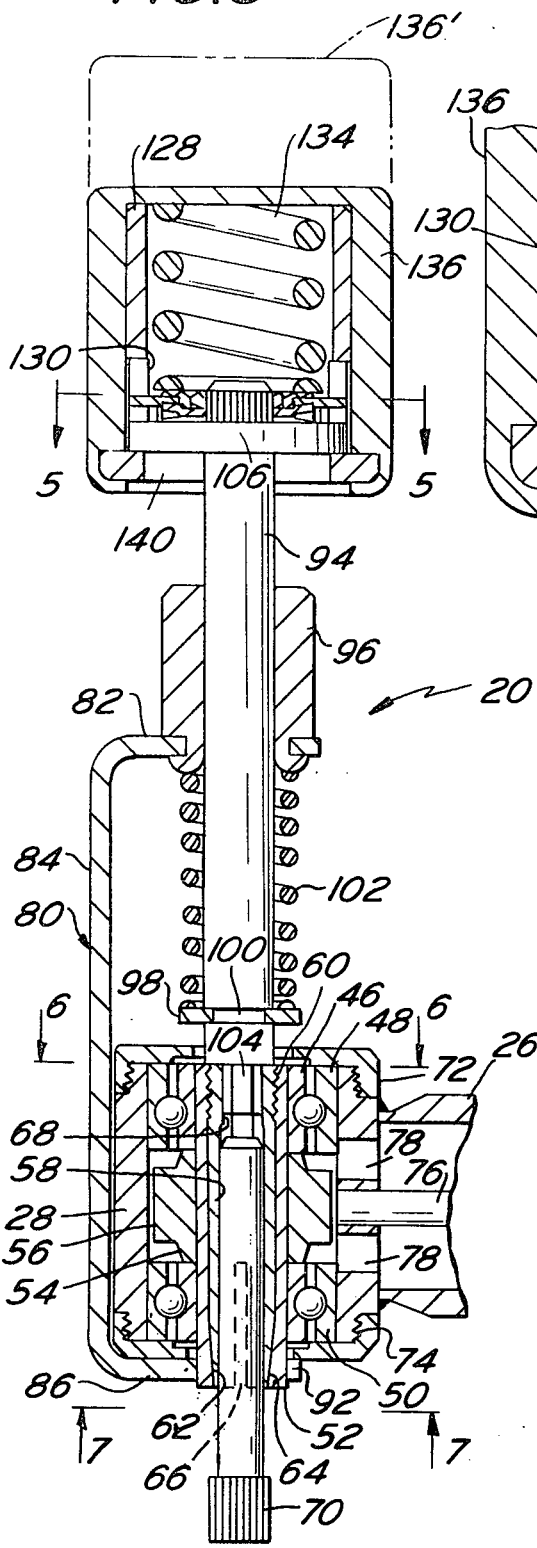
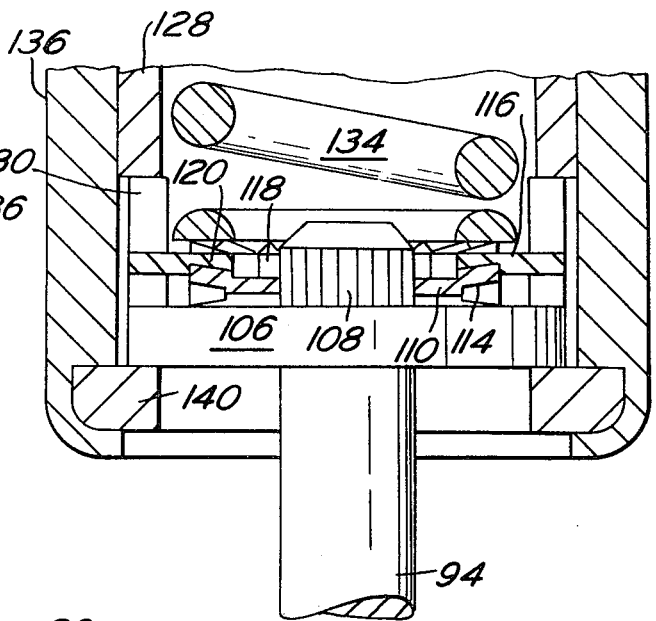
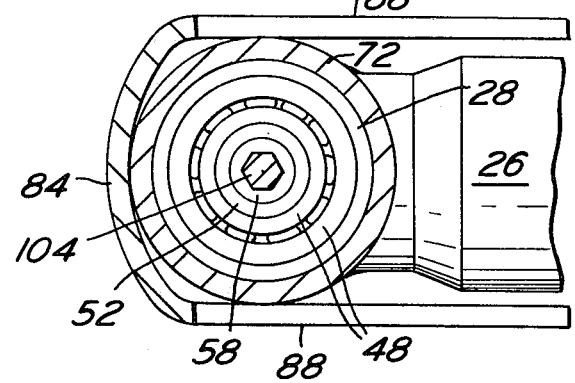

COLLET WRENCH

This invention relates to a collet wrench, and more particularly, to a wrench adapted to secure a bur in an air driven dental handpiece.

It is now common practice in the dental art to supply rotative power to a dental handpiece through the use of an air driven rotor or turbine. Extremely high speeds have been attained utilizing pneumatically driven dental handpieces. A major improvement in air driven dental handpieces has been the provision of a bur-securing collet that is threadedly secured in the rotor shaft of the air turbine rotor. The collet has compressible jaws on the lower end and is threadedly secured to the rotor shaft at the upper end. A bur is secured in or released from the collet by threadedly advancing or retracting the collet relative to the rotor shaft, which in turn compresses or opens the jaws of the collet. The threaded collet and its method of securing a dental bur in the handpiece are disclosed in U.S. Pat. No. 3,120,706.

Since the invention of U.S. Pat. No. 3,120,706 was made, various attempts have been made to improve the wrench assembly for advancing and retracting the collet relative to the rotor shaft. Some of these improvements are disclosed in U.S. Pat. Nos. 3,499,223 and 3,325,899, and in U.S. application Ser. No. 476,749, filed June 5, 1974, the disclosure of which is incorporated by reference herein.

It has now been found that all of the collet wrenches previously known to the art have had one disadvantage in common. Thus, all of these wrenches have a knob for rotating the shaft that is received in the collet, which knob is keyed to the shaft, or otherwise secured, as by a pressed fit. It has further been found that when a man rotates this knob, he will apply, on the average, a given force to the collet to threadedly secure it in place when a bur has been inserted in the collet. Likewise, a woman utilizing the same wrench will supply a substantially lower force to the wrench, and accordingly a substantially lower locking force on the collet securing the bur. In order to increase the force that a woman applies to the collet wrench, it is necessary to increase the diameter of the knob securing the shaft for locking the collet in place. However, if the knob diameter is increased, a man utilizing the wrench will in turn apply a substantially greater force to the collet.

Since it is inconvenient to have separate wrenches for men and women, and since both men and women will use the same handpiece and wrench, a problem has arisen. Thus, if the knob is made too large, a man will apply too great a force to the collet, thereby either stripping the threads or securing the bur in place with too great a force, making it difficult to remove the bur. Alternatively, if the knob diamater is too small, a woman will not supply sufficient force to the collet, and the bur may become inadvertently loosened and fall out, or will not be held securely in place, thereby resulting in non-concentric rotation of the bur during use.

All of the problems of proper force on the collet are eliminated by utilizing the collet wrench of this invention. Thus, the knob is made sufficiently large to enable either a man or a woman to apply the correct force for securing the bur in place, while at the same time, not applying too great a force to damage the collet or lock the bur in place to the extent that it can not easily be removed. The collet wrench of this invention includes a slip mechanism whereby once the proper force has been applied, no greater force can be applied to the collet.

Although the wrench of this invention was specifically developed for use as a collet wrench, it has been found that it can be used in many other industrial applications. Thus, utilizing the teachings of this invention, a torque wrench can be made which can be used in any area where the prior art torque wrenches have been used. In the prior art torque wrenches the driving handle is keyed to the wrench shaft. A gauge is formed on the handle to indicate the amount of torque that is being applied. Utilizing the wrench of this invention, the amount of torque that will be applied can be preset by the judicious selection of a spring, and accordingly, the preset torque will always be applied. There is no need to refer to gauges, since it will be known by the user that the same predetermined torque will always be applied.

It is accordingly an object of this invention to provide a novel collet wrench for use on an air driven dental handpiece.

It is another object of this invention to provide a novel torque wrench.

These and other objects of this invention are accomplished by providing a wrench comprising a shaft, said shaft having one end configured to be received in a threaded, rotatable securing device, the other end of said shaft having a disc secured thereto, said disc having teeth formed in the upper surface thereof, a second disc overlying said first disc, and being rotatably mounted on said shaft, said second disc having teeth which are complementary with the teeth in said first disc, spring means urging said second disc into contact with said first disc, and means for rotating said second disc relative to said first disc.

Other objects and many of the attendant advantages of this invention will be readily appreciated as the same becomes better understood by reference to the following detailed description when considered in connection with the accompanying drawings wherein:

FIG. 1 is an exploded side elevational view showing the collet wrench of this invention and a handpiece on which the collet wrench may be used;

FIG. 2 is a perspective view showing the collet wrench of this invention as placed on the dental handpiece of FIG. 1;

FIG. 3 is a sectional view showing the collet wrench of this invention as secured in place;

FIG. 4 is an exploded perspective view showing the elements forming the upper part of the collet wrench of this invention;

FIG. 5 is a sectional view taken along the line 5—5 of FIG. 3;

FIG. 6 is a sectional view taken along the line 6—6 of FIG. 3;

FIG. 7 is a sectional view taken along the line 7—7 of FIG. 3;

FIG. 8 is an enlarged sectional view of the upper portion of the collet wrench of FIG. 3; and FIG. 9 is an enlarged sectional view showing the meshing of the teeth of the two discs of the wrench of this invention.

Referring now in greater detail to the various figures of the drawings wherein like reference character refer to like parts, a collet wrench embodying the present invention is generally shown at 20 in FIG. 1. An air driven dental handpiece on which the wrench 20 may be used is also generally shown at 22 in FIG. 1.

The dental handpiece 22 includes a hollow handle 24 having an angled neck 26 and a turbine housing 28 mounted perpendicularly to neck 26. An adaptor nut 30 is threadedly secured on handle 24 and a connector sleeve 32 is threadedly secured on adaptor nut 30. The connector sleeve 32 is used for connecting external sources of air 34, light transmitting fibers 36 and water 38 with the handpiece. A collar 40 is slideably mounted on neck 26, and supports water spray tubes 42. An internal fiber optic light system terminates in tubes 44.

Referring to FIG. 3, it is seen that turbine housing 28 includes a turbine cartridge 46. Turbine cartridge 46 comprises upper ball bearing 48, lower ball bearing 50, a rotor shaft 52, a hub 54 keyed to the rotor shaft and blades 56 projecting from hub 54. A hollow collet 58 is threadedly secured within rotor shaft 52 by threads 60.

The rotor shaft includes an inwardly tapering wall 62 at its bottom. Likewise, the exterior wall of collet 58 is inwardly tapering, as shown at 64 in FIG. 3. The collet includes a pair of diametrically opposed slots (one shown in phantom at 66 in FIG. 3), which slots divide the collet into a pair of jaws. The top of collet 58 is provided with a bore 68 of non-circular cross-section. In the embodiment of the invention shown, the bore has a hexagonal cross-section. As will be explained hereinafter, the rotation of the collet 58 in rotor shaft 52 causes the compression of the jaws of the collet, thereby securing the shaft of dental bur 70 within the collet.

Turbine housing 28 is provided with a threadedly secured upper end cap 72 and a threadedly secured lower end cap 74. As seen in FIG. 3, the outer races of ball bearings 48 and 50 are contacted by the inner surfaces of the end caps 72 and 74. However, each end cap is provided with an internal recess whereby the end caps will not be contacted by the inner races of the ball bearings. Accordingly, the rotor shaft 52, which is keyed to the inner races, is freely rotatable along with the inner races between the end caps 72 and 74.

As is apparent from FIG. 3, the turbine cartridge 46 comprises the rotor shaft, the ball bearings, the collet and the rotor. This cartridge is removable as a unit from the turbine housing 28 by the removal of the end caps 72 and 74, whereby the turbine cartridge may be slid from the turbine housing. The air for rotating the rotor blades 56, and in turn, the rotor shaft 52 with its secured collet 58, is furnished by air conduit 76. The exhaust air leaves through ports 78 in turbine housing 28, and then back through neck 26 and handle 24.

To the extent described, the dental handpiece 22, including the elements of turbine housing 28, is the same as that disclosed in U.S. application Ser. No. 476,759, filed June 5, 1974, the disclosure of which has been incorporated by reference herein. This specific handpiece has been shown by way of example. The collet wrench of this invention is adapted for use on any air driven dental handpiece having a threaded collet of the type described, such as those shown in the aforementioned United States Patents. The collet wrench 20 forming this invention will now be described.

Wrench 20 includes a frame 80 having an upper leg 82, a vertical leg 84 and a lower leg 86. A pair of flanges 88 project from leg 84 (FIGS. 2 and 6). Lower leg 86 includes an inwardly extending cut 90 that has a pair of straight sides 92 (FIG. 7). As seen in FIG. 7, the rotor shaft 52 has a square cross section at its lower end, and the straight sides 92 act as a wrench to grasp the rotor shaft at said lower end when the device 20 is placed on the turbine housing 28. As will be explained hereinafter, the straight sides 92 prevent rotation of the rotor shaft 52 when the collet 58 is being moved relative to the rotor shaft.

A collet advancing shaft 94 is rotatably mounted in bushing 96, which is in turn secured in upper leg 82 of frame 80 (FIG. 3). As will be explained hereinafter, shaft 94 is also vertically reciprocable in bushing 96. A split ring 98 is secured on shaft 94 in an annular groove 100 in the shaft. A compression spring 102 is positioned around shaft 94 and bears against the upper side of ring 98 and the lower side of bushing 96. The bottom of shaft 94 has a reduced head 104 of non-circular cross-section. The cross-section of head 104 is the same as the upper bore 68 of collet 58, and is slightly smaller in size than the bore of the collet so that it can be inserted in said bore.

A disc 106 is secured on shaft 94 adjacent the top thereof. The top of shaft 94 is provided with a plurality of spaced vertical slots 108. A clutch plate 110 having a central opening 112 is secured on shaft 94 over disc 106. The opening 112 is approximately the same diameter as the diameter of the shaft 94, and the securement of the clutch plate 110 occurs by the frictional engagement of the slotted top 108 in opening 112. As seen in FIG. 4, clutch plate 110 includes a plurality of teeth 114 which extend around its entire outer surface.

Referring still to FIG. 4, a drive plate 116 having a central opening 118 is provided. Drive plate 116 includes a plurality of teeth 120 which extend around opening 118. The perimeter of drive plate 116 includes a plurality of equally spaced slots 122.

In the assembly of the wrench 20, as best seen in FIG. 8, the drive plate 116 is placed over the top of shaft 94, with the teeth 120 engaged in the teeth 114. As further seen in FIG. 8, since the opening 118 in drive plate 116 is substantially larger than the diameter of shaft 94, the drive plate 116 can rotate relative to the shaft 94. As seen in FIG. 9, teeth 114 and teeth 120 each include a relatively long gradual inclined surface 124 and a relatively short, sharply inclined surface 126. The angle of surface 124 is substantially smaller than the angle of surface 126. The teeth 114 and 120 extend in the same direction and at identical angles. Thus, in the assembled condition of the wrench, these teeth are enmeshed, as seen in FIGS. 3, 8 and 9.

Referring again to FIG. 4, it is seen that the wrench 20 further includes a hollow drive cylinder 128 having equally spaced legs 130 projecting downwardly at the bottom thereof. The upper portion of the outer surface of the drive cylinder 128 includes a plurality of slots 132. Referring to FIGS. 3 and 8, it is seen that in the assembled condition of wrench 20, cylinder 128 is positioned above plates 110 and 116, and legs 130 are engaged in slots 122 of plate 116 (see also FIG. 5).

A compression spring 134 is placed within cylinder 128, with the lower end of the spring abutting teeth 120 on drive plate 116. A hollow cylindrical knob 136 is placed over cylinder 128, and is held in place by the frictional engagement of the slotted portion 132 of cylinder 128 against the interior wall of knob 136. As seen in FIG. 2, 136 has a knurled outer surface to aid in grasping the same. As seen in FIG. 3, knob 136 includes a lower annular groove, and a retainer ring 140 is mounted in this groove. In the assembled condition of the wrench, the spring 134 tends to push disc 106 downwardly, and the disc in turn bears against retainer ring 140.

Referring to FIG. 3, the wrench 20 is used by grasping knob 136 and lifting it vertically upward to the position shown at 136'. This in turn will lift the shaft 94 vertically to the extent that the lower end 104 of the shaft is spaced a distance from leg 86 of frame 80 which is greater than the height of turbine housing 28. The lifting of the knob 136 is against the urging of spring 102.

With the knob 136 so lifted, and the consequent lifting of shaft 94, the frame 80 can be placed over turbine housing 28, with the bottom of rotor shaft 52 being received in slot 90 (FIG. 7). It should be kept in mind that the rotor shaft 52 is freely rotatable, and thus the insertion of the rotor shaft in the slot is easily accomplished. With the rotor shaft so engaged, the knob 136 is released. Spring 102, acting against split ring 98, then forces the shaft 94 downwardly so that the end 104 of the shaft is received in hexagonal bore 68 of the collet. The shaft 94 is freely rotatable, and accordingly it can easily be engaged in the top of the collet.

As explained in the aforementioned United States Patents and aforementioned U.S. application Ser. No. 476,749, when the collet 58 is in its upper position, the jaws formed at slots 66 are open. A dental bur 70 can then be inserted between the jaws and subsequently secured in place by the threaded advancement of the collet downwardly relative to rotor shaft 52. Thus, when the collet is rotated relative to the rotor shaft, at threads 60, the tapered jaws 64 are compressed by the tapered wall 62 of the rotor shaft 52.

In order to rotate the collet relative to the rotor shaft, the rotor shaft must be maintained in a stationary condition. This is accomplished by the engagement of the outer surface of the rotor shaft with the jaws formed by the slot 90 of leg 86. The engagement of the flanges 88 (FIGS. 6 and 7) with the turbine housing 28 prevents any substantial rotation of the frame once it has been secured in place, and accordingly, there can be no substantial rotation of the rotor shaft once it is engaged in the jaws of the lower leg 86. The shaft 94 is then rotated through the knob 136 to threadedly advance the collet downwardly in the rotor shaft in order to secure the bur 70 in place.

The rotating mechanism for the shaft 94 will now be explained. Spring 134 engages the teeth 120 of plate 116 with the teeth 114 of plate 110. Accordingly, when the knob 136 is rotated, there will be a consequent rotation of shaft 94, since the plate 110 is keyed to the shaft. This in turn will rotate the collet along threads 60. The rotor shaft 52 is maintained in a stationary condition by the jaws of lower leg 86.

Eventually, the collet will tightly secure the dental bur 70 in place. When this occurs, continued rotation of the knob 136 will cause the plate 116 to rotate relative to the plate 110. Thus, referring to FIG. 9, it is seen that the inclined portion of the teeth 120 can slide over the inclined portion of the teeth 114. Until there is any resistance to the rotation of the shaft, which occurs when the collet is tightly secured in place, the spring 134 maintains the engagement between the teeth of plate 116 and plate 110. However, once the collet is secured in its predetermined maximum lower position, the continued rotation of the knob 136 overcomes the force of the spring 134, and accordingly the teeth of the upper plate 116 will ride over the teeth of the lower plate 110. The amount of force needed to accomplish this riding over feature is directly dependent on the strength of the spring 134. Thus, the lighter the force of the spring, the sooner the riding over will occur. By the judicious selection of the spring force, the amount of tightness on the collet can be regulated.

When the collet is tightened on the dental bur 70, the knob 136 is rotated in a clock wise direction, as viewed in FIGS. 2 and 3. When it is desired to remove the bur, the collet 58 must be raised relative to the rotor shaft 52, so that the jaws are opened. In order to accomplish this, the knob 136 is rotated in a counter-clock wise direction. When this occurs, the spring 134 keeps the teeth of the plates 116 and 110 firmly engaged. Furthermore, because of the sharper angle 126 of the teeth, the counter-clock wise rotation of the knob will not permit the upper teeth to ride over the lower teeth. Accordingly, the collet will always be rotated whenever the knob 136 is rotated in a counter-clock wise direction. This causes the collet to be raised relative to the rotor shaft, causes the jaws of the collet to open, and permits the dental bur 70 to drop from the collet.

The transmission of the rotational power of the knob 136 to the shaft should be readily apparent from FIG. 3. Thus, the knob is keyed to the drive cylinder 128 by a pressed fit. When the knob is rotated, the cylinder 128 will likewise be rotated. The cylinder has the lower legs 130 engaged in the slots 122 of the plate 116. Accordingly, when the cylinder is rotated by the knob 136, the plate 116 will likewise be rotated.

Since the spring 134 maintains contact between the teeth of plate 116 and the plate 110, when the plate 116 is first rotated, the plate 110 will likewise be rotated. Since the plate 110 is keyed to the shaft 94, the rotation of the plate 110 in turn rotates the shaft 94.

As pointed out above, through the judicious selection of spring sizes, the maximum force applied to the collet can easily be set. Utilizing the prior art wrenches, when a knob for the wrench had a diameter of approximately ¼ inch, it was found that a woman utilizing the handpiece would apply a torque of approximately ½ pound inch. A man utilizing the same wrench would apply a torque to the collet of 1 ½ pound inches. It has now been determined that the maximum effective torque to be applied to the collet is 1 pound inch. The knob is made of a diameter which is sufficiently large for a woman to use to obtain this torque. By way of example, the outer diameter of the knob 136 is ½ inch. By way of further non-limiting example, in order to obtain the 1 pound inch of torque, the spring 134 has a rate of 67 pounds per inch, a free length of 0.380 inch and a wire diameter of 0.040 inch. The load at which the upper plate 116 slips relative to the lower plate 110 is 10 pounds, and the length of the spring at this load is 0.230 inch.

The foregoing ratings are solely by way of example. Obviously, these parameters can be varied at will in order to obtain the desired preset torque. It is thus seen that the wrench of this invention can readily be used on any air driven dental handpiece wherein the collet is threadedly secured to the rotor shaft. Any mechanism can be used for preventing rotation of the rotor shaft, such as the slotted leg 86 shown, or the mechanism shown in aforementioned U.S. application Ser. No. 476,749. If it is desired to reduce the overall height of the wrench, the bushing 96 (FIG. 3) can be inverted so that it is placed below the upper leg 82.

Although the invention has been particularly described with reference to a collet wrench for a dental handpiece, it should be understood that the teachings of this invention can be used to make a torque wrench for use where any of the prior art torque wrenches have been used. Thus, a lever arm can extend from the knob 136 in order to utilize the wrench for supplying extremely large torques in industrial applications. Instead of having the lower head 104, any of the socket heads used in prior art torque wrenches can be used. Likewise, when the wrench is used as an industrial torque wrench, it will be unnecessary to have the frame 80. The wrench can be constructed, through the judicious selection of spring 134, to apply a predetermined torque of substantially any magnitude.

A user of the wrench of this invention can readily determine when the proper torque has been applied since the knob will vibrate when plate 116 slides relative to plate 110, and in addition, there will be a distinct clicking sound by the dropping of the teeth in place. The force of spring 134 is sufficient to permit the loosening of any threaded mechanism which has been tightened by the wrench.

Without further elaboration, the foregoing will so fully illustrate our invention that others may, by applying current or future knowledge, readily adapt the same for use under various conditions of service.

What is claimed as the invention is:

1. A wrench adapted to be hand-held comprising a shaft, said shaft having one end configured to be received in a threaded, rotatable securing device, said end being adapted to cause the rotating of said securing device when said end is rotated, the other end of said shaft having a first disc secured thereto, said first disc having teeth formed in the upper surface thereof, a second disc overlying said first disc, and being rotatable relative to said shaft, said second disc having teeth which are complementary with the teeth in said first disc on the under surface thereof, spring means urging said second disc into contact with said first disc, and means for rotating said second disc, said rotating means comprising a cylinder, said cylinder having a plurality of legs projecting downwardly therefrom, said legs being engaged in slots in said second disc, said spring means having a force sufficient to cause the rotation of said first disc when said second disc is rotated, and said spring means permitting rotation of said second disc relative to said first disc when a predetermined rotational force has been applied to said securing device.

2. The wrench of claim 1 wherein said rotating means further comprise a knob, said knob being secured on said cylinder.

3. The wrench of claim 1 wherein said teeth on said first disc and on said second disc have two inclined surfaces, one of said surfaces having a smaller angle than the other of said surfaces, said second disc being adapted to rotate relative to said first disc by the disengagement and reingagement of said teeth when said second disc is rotated in a first direction which causes the sliding of said second disc relative to said first disc along said smaller angle surface.

4. The wrench of claim 3 wherein said second disc will rotate said first disc when said second disc is rotated in a direction opposite that which causes the sliding of said second disc relative to said first disc, said rotating in said opposite direction causing the engagement of said teeth at said larger angle surfaces.

5. The wrench of claim 1 and further including a frame, said shaft being rotatable in said frame, said frame having means thereon for preventing rotation of a rotatable element in which said securing device is threadedly secured.

6. A wrench adapted to be hand-held comprising a frame, said frame having means thereon for preventing rotation of a rotatable member, a shaft rotatably secured in said frame, said shaft having one end configured to be received in a threaded rotatable securing device, said securing device being threadedly secured on said rotatable member, said end being adapted to cause the rotation of said securing device when said end is rotated, the other end of said shaft having a first disc secured thereto, a second disc overlying said first disc, and being rotatable relative to said shaft, said second disc being urged into contact with said first disc by spring means, means on the abutting surfaces of said discs to cause the interlocking of said discs whereby the rotation of the second disc will cause the rotation of said first disc, and means for rotating said second disc, said rotating means comprising a cylinder, said cylinder having a plurality of legs projecting downwardly therefrom, said legs being engaged in slots in said second disc, said spring means having a force sufficient to cause the rotation of said first disc when said second disc is rotated, and said spring means permitting rotation of said second disc when a predetermined rotational force has been applied to said securing device.

7. The wrench of claim 6 wherein said frame includes a vertical leg and an upper horizontal leg projecting therefrom, said shaft being rotatably mounted in said upper horizontal leg.

8. The wrench of claim 7 wherein said frame further includes a lower horizontal leg, said rotation preventing means comprising a slot in said lower horizontal leg, said slot having a pair of jaws configured to grasp flattened surfaces on said rotatable member to prevent rotation of said rotatable member.

9. The wrench of claim 6 wherein said shaft is also vertically reciprocable in said frame, and second spring means urging said shaft downwardly relative to said frame.

10. The wrench of claim 6 wherein said engageable means on said discs comprise complementary teeth formed in the upper and lower surfaces of said first and second discs, respectively.

11. The wrench of claim 6 wherein said rotating means further comprise a knob, said knob being secured on said cylinder.

12. The wrench of claim 10 wherein said teeth on said disc and on said second disc have two inclined surfaces, one of said surfaces having a smaller angle than the other of said surfaces, said second disc being adapted to rotate relative to said first disc by the disengagement and reingagement of said teeth when said second disc is rotated in a first direction which causes the sliding of said second disc relative to said first disc along said smaller angle surface.

13. The wrench of claim 12 wherein said second disc will rotate said first disc when said second disc is rotated in a direction opposite that which causes the sliding of said second disc relative to said first disc, said rotating in said opposite direction causing the engagement of said teeth at said larger angle surfaces.

* * * * *